United States Patent [19]

Lesher et al.

[11] Patent Number: 4,560,753
[45] Date of Patent: * Dec. 24, 1985

[54] 2-SUBSTITUTED-PYRIDO[2,3-D]PYRIMIDIN-5(8H)-ONES

[75] Inventors: George Y. Lesher, Schodack; Baldev Singh; Stanley C. Laskowski, both of East Greenbush, all of N.Y.

[73] Assignee: Sterling Drug Inc., New York, N.Y.

[*] Notice: The portion of the term of this patent subsequent to Feb. 21, 2001 has been disclaimed.

[21] Appl. No.: 541,199

[22] Filed: Oct. 12, 1983

Related U.S. Application Data

[63] Continuation-in-part of Ser. No. 439,361, Nov. 5, 1982, Pat. No. 4,432,981.

[51] Int. Cl.$^4$ .................. C07D 487/04; A61K 31/505
[52] U.S. Cl. ..................................... 544/279; 514/258; 544/329
[58] Field of Search ......................................... 544/279

[56] References Cited

U.S. PATENT DOCUMENTS

| | | | |
|---|---|---|---|
| 3,642,797 | 2/1972 | Lesher | 544/282 |
| 3,873,545 | 3/1975 | Osselaere et al. | 544/279 |
| 3,992,380 | 11/1976 | Lesher et al. | 544/279 |
| 4,018,770 | 4/1977 | Lesher et al. | 544/279 |
| 4,380,632 | 4/1983 | Steffen | 544/279 |
| 4,432,981 | 2/1984 | Lesher et al. | 424/251 |

OTHER PUBLICATIONS

Matsumoto et al, [Japanese Kokai 78 18,600, published Feb. 20, 1978; C.A., 89, 24,351d (1978)].

*Primary Examiner*—George F. Lesmes
*Assistant Examiner*—S. A. Gibson
*Attorney, Agent, or Firm*—Robert K. Bair; B. Woodrow Wyatt; Paul E. Dupont

[57] ABSTRACT

2-Q-6-Q'-8-R-pyrido[2,3-d]pyrimidin-5(8H)-ones (I), where Q is 4(or 3)-hydroxyphenyl, 4(or 3)-methoxyphenyl, 4(or 3)-pyridinyl or 4(or 3)-pyridinyl having one or two lower-alkyl substituents, R' is hydrogen or alkyl having one to four carbon atoms, Q is hydrogen, amino or nitro, and R is alkyl having from one to four carbon atoms, $CH(C_2H_5)_2$, $(CH_2)_n=CHCH_2$ where n is 1 or 2, or Y—Z where Y is alkylene having from two to four carbon atoms and having its connecting linkages on different carbon atoms and Z is hydroxy, $OR_1$ or $NR_1R_2$ where $R_1$ and $R_2$ are each methyl or ethyl, or acid-addition salts thereof, and their preparation are shown. Also shown is the cardiotonic use of I where Q is 4(or 3)-hydroxyphenyl, 4(or 3)-pyridinyl or 4(or 3)-pyridinyl having one or two lower-alkyl substituents and Q' is hydrogen or amino.

5 Claims, No Drawings

2-SUBSTITUTED-PYRIDO[2,3-D]PYRIMIDIN-5(8H)-ONES

CROSS-REFERENCE TO RELATED APPLICATION

This application is a continuation-in-part of copending application Ser. No. 439,361, filed Nov. 5, 1982, now U.S. Pat. No. 4,432,981, issued Feb. 21, 1984.

BACKGROUND OF THE INVENTION (a) Field of the Invention

This invention relates to processes for preparing 2-(pyridinyl or hydroxyphenyl)8-substituted-pyrido[2,3-d]pyrimidin-5(8H)-ones and to 8-unsubstituted intermediates therefor.

(b) Information Disclosure Statement

Lesher and Singh [U.S. Pat. No. 3,992,380, issued Nov. 16, 1976] show as antibacterial agents, 5,8-dihydro-8-(lower-alkyl)-5-oxo-2-Q-4-$R_2$-6-Z-pyrido[2,3-d]pyrimidines where Z is carboxy or lower-carbalkoxy, $R_2$ is hydrogen or lower-alkyl and Q is 4(or 3)-pyridinyl or 4(or 3)-pyridinyl having one or two lower-alkyl substituents. Said antibacterial agents are prepared by heating di-(lower-alkyl) N-(2-Q-6-$R_2$-4-pyrimidinyl)aminomethylenemalonate to produce 5,8-dihydro-5-oxo-2-Q-4-$R_2$-6-(lower-carbalkoxy)-pyrido[2,3-d]pyrimidine where Q and $R_2$ are as defined above, reacting the latter with a lower-alkylating agent to produce the corresponding 8-(lower-alkyl) compound and hydrolyzing this compound to produce the 6-carboxy derivative.

Lesher and Singh [U.S. Pat. No. 4,018,770, issued Apr. 19, 1977] disclose and claim, inter alia, cyclic alkylidenyl N-[2-(pyridinyl)-4-pyrimidinyl]aminomethylenemalonate, e.g., isopropylidenyl N-[2-(4-pyridinyl)-4-pyrimidinyl]aminomethylenemalonate, alternatively named 2,2-dimethyl-5-<{[2-(4-pyridinyl)-4-pyrimidinyl]amino}methyl>-1,3-dioxane-2,4-dione, which are used herein as intermediates.

Osselaere et al. [U.S. Pat. No. 3,873,545, issued Mar. 25, 1975], disclose, inter alia, 2-(3-pyridinyl or 4-pyridinyl)-3,4-dihydropyrido[2,3-d]pyrimidin-4-one as having spasmolytic and diuretic activities.

Matsumoto et al [Japanese Kokai 78 18,600, published Feb. 20, 1978; C.A. 89, 24,351d (1978)] show 8-ethyl-2-(1-piperazinyl)pyrido[2,3-d]pyrimidin-5-one hydrochloride as having analgesic activity in mice and antiinflammatory activity in rats.

Lesher [U.S. Pat. No. 3,642,797, issued Feb. 15, 1972] shows the preparation of a 4H-pyrido[1,2-a]pyrimidin-4-one by heating a cyclic alkylidenyl 2-pyridinylaminomethylenemalonate and also the preparation of a 4-hydroxyquinoline by heating a cyclic alkylidenyl anilinomethylenemalonate as well as the preparation of a 4-hydroxyquinoline by heating an aniline with a mixture of a trialkyl orthoformate and a cyclic alkylidenyl malonate.

SUMMARY OF THE INVENTION

The invention in a process aspect resides in the process which comprises heating cyclic alkylidenyl N-(2-Q-6-R'-4-pyrimidinyl)aminomethylenemalonate (II) to produce 2-Q-4-R'-pyrido[2,3-d]pyrimidin-5(8H)-one (III) and reacting III with an ester of the formula R-An (IV) to produce 2-Q-4-R'-6-Q'-8-R-pyrido[2,3-d]pyrimidin-5(8H)-one (I), where Q, Q', R, R' and An are defined below.

The invention in another process aspect resides in the process which comprises nitrating 2-Q-4-R'-8-R-pyrido[2,3-d]pyrimidin-5(8H)-one (I where Q' is hydrogen) to produce 2-Q-4-R'-6-nitro-8-R-pyrido[2,3-d]pyrimidin-5(8H)-one (I where Q' is $NO_2$) and reacting the 6-nitro compound with a reducing agent to produce 2-Q-4-R'-6-amino-8-R-pyrido[2,3-d]pyrimidin-5(8H)-one (I where Q' is amino).

In a composition of matter aspect, the invention resides in 2-Q-4-R'-pyrido[2,3-d]pyrimidin-5(8H)-ones (III), useful as intermediates, where Q and R' are defined hereinbelow.

DETAILED DESCRIPTION INCLUSIVE OF PREFERRED EMBODIMENTS

A process aspect of the invention resides in the process for producing the compound of formula I where Q' is hydrogen which comprises heating a lower-cyclicalkylidenyl N-(2-Q-6-R'-4-pyrimidinyl)aminomethylenemalonate of the formula II

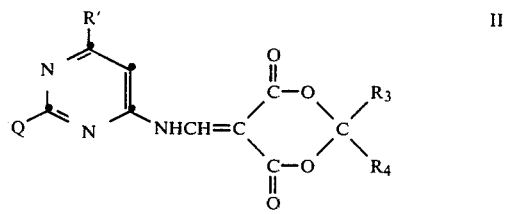

to produce a 2-Q-4-R'-pyrido[2,3-d]pyrimidin-5(8H)-one of formula III

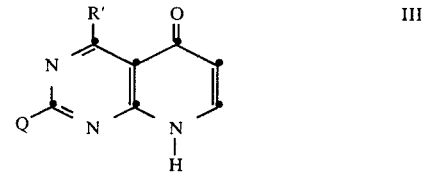

and reacting the compound of formula III or alkali or alkaline earth metal salt thereof with an alkylating agent of the formula R-An (IV) to produce 2-Q-4-R'-6-Q'-8-R-pyrido[2,3-d]pyrimidin-5(8H)-one having formula I

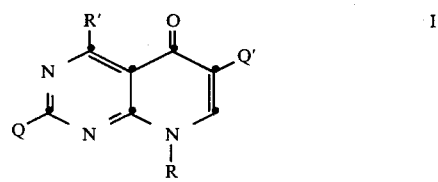

where Q' is hydrogen, R' is hydrogen or alkyl having from one to four carbon atoms, R is alkyl having from one to four carbon atoms, $CH(C_2H_5)_2$, $(CH_2)_nCH=CH_2$ where n is 1 or 2, or Y—Z where Y is alkylene having from two to four carbon atoms and having its connecting linkages on different carbon atoms and Z is hydroxy, $OR_1$ or $NR_1R_2$ where $R_1$ and $R_2$ are each methyl or ethyl, Q is 4(or 3)-methoxyphenyl, 4(or 3)-pyridinyl or 4(or 3)-pyridinyl having one or two lower-alkyl substituents, $R_3$ and $R_4$ are each lower-alkyl having from one to four carbon atoms and An is a leaving group corresponding to the anion of a strong inorganic acid or an organic sulfonic acid, and reacting the compound of formula I where Q' is hydrogen and Q is 4(or 3)-methoxyphenyl with an agent capable of converting methoxyphenyl to hydroxyphenyl. A preferred embodiment of this process aspect of the invention utilizes in the first step the compound of formula II where $R_3$ and $R_4$ are each methyl, R' is hydrogen or methyl and Q is 4(or 3)-pyridinyl, and using in the second step an alkali metal salt of the compound of formula III and R-An where R is ethyl, n-propyl, n-butyl, allyl, 3-butenyl and 1-ethylpropyl and An is chloride, bromide, iodide or sulfate.

Another process aspect of the invention resides in the process which comprises reacting 2-Q-4-R'-8-R-pyrido[2,3-d]pyrimidin-5(8H)-one (I where Q' is hydrogen) with a nitrating agent to produce 2-Q-4-R'-6-nitro-8-R-pyrido[2,3-d]pyrimidin-5(8H)-one (I where Q' is nitro) and reducing said 6-nitro compound to produce the corresponding 2-Q-4-R'-6-amino-8-R-pyrido[2,3-d]pyrimidin-5(8H)-one (I where Q' is amino), where R' and R have the meanings given above for formula I and Q is 4(or 3)-pyridinyl or 4(or 3)-pyridinyl having one or two lower-alkyl substituents. Preferred embodiments of this process aspect of the invention result in the preparation of the 2-Q-4-R'-6-amino-8-R-pyrido[2,3-d]pyrimidin-5(8H)-ones where Q is 4(or 3)-pyridinyl, R' is hydrogen or methyl and R is ethyl, n-propyl, n-butyl, allyl, 3-butenyl and 1-ethylpropyl.

A composition of matter aspect of the invention resides in a 2-Q-4-R'-pyrido[2,3-d]pyrimidin-5(8H)-one having formula III

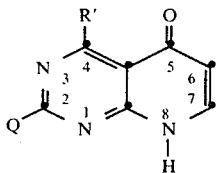

or acid-addition or alkali or alkaline earth metal salt thereof, where Q is 4(or 3)-hydroxyphenyl, 4(or 3)-methoxyphenyl, 4(or 3)-pyridinyl or 4(or 3)-pyridinyl having one or two lower-alkyl substituents, and R' is hydrogen or alkyl having from one to four carbon atoms. The compounds of formula III are useful as intermediates for preparing the corresponding 2-Q-4-R'-6-Q'-8-R-pyrido[2,3-d]pyrimidin-5(8H)-ones of formula I where Q' is hydrogen. The compounds of formula I, which are useful as cardiotonics, are disclosed and claimed in said copending application Ser. No. 439,361. Preferred embodiments are those of formula III where R' is hydrogen or methyl, and Q is 4(or 3)-pyridinyl.

The terms "lower-alkyl", as used herein as one or two substituents of (4 or 3)-pyridinyl, and "alkyl having from one to four carbon atoms", as used herein, e.g., as the one of the meanings for R or as the meaning for R', $R_3$ or $R_4$ means alkyl radicals having from one to four carbon atoms which can be arranged as straight or branched chains, illustrated by methyl, ethyl, n-propyl, isopropyl, n-butyl, 2-butyl or isobutyl.

Illustrative of Q in formulas I, II or III where Q is 4- or 3-pyridinyl having one or two lower-alkyl substituents are the following: 2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl), 2,3-dimethyl-4-pyridinyl, 2,6-dimethyl-4-pyridinyl, 2-ethyl-4-pyridinyl, 2-isopropyl-4-pyridinyl, 2-n-butyl-4-pyridinyl, 2,6-diethyl-4-pyridinyl, 2,6-diethyl-3-pyridinyl, 2,6-diisopropyl-4-pyridinyl, and the like.

The compounds of the invention having formula I or III are useful both in the free base and in the form of acid-addition salts, and both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically acceptable salts, that is, referring to the compounds of formula I, salts whose anions are relatively innocuous to the animal organism in pharmaceutical doses of the salts, so that the beneficial cardiotonic properties inherent in the free base form of the cardiotonically active compounds of the invention are not vitiated by side effects ascribable to the anions. In practicing the invention, it is convenient to use the free base form; however, appropriate pharmaceutically acceptable salts within the scope of the invention are those derived from mineral acids such as hydrochloric acid, sulfuric acid, phosphoric acid and sulfamic acid; and organic acids such as acetic acid, citric acid, lactic acid, tartaric acid, methanesulfonic acid, ethanesulfonic acid, benzenesulfonic acid, p-toluenesulfonic acid, cyclohexylsulfamic acid, quinic acid, and the like, giving the hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate, respectively.

The acid-addition salts of said basic compounds of formula I or III are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically acceptable salts of said basic compounds are preferred, all acid-addition salts are within the scope of our invention. All acid-addition salts are useful as sources of the free base form even if the particular salt per se is desired only as an intermediate product as for example when the salt is formed only for purposes of purification or identification, or when it is used as an intermediate in preparing a pharmaceutically acceptable salt by ion exchange procedures.

Other useful salts of the intermediate compounds of formula III are their alkali metal salts, e.g., sodium or potassium, or the alkaline earth metal salts, e.g., calcium, which are useful in said process for preparing the compounds of formula I where Q' is hydrogen.

The molecular structures of the compounds of the invention were assigned on the basis of evidence provided by infrared, nuclear magnetic resonance and mass spectra, and by the correspondence of calculated and found values for the elemental analyses.

The manner of making and using the instant invention will now be generally described so as to enable a person skilled in the art of pharmaceutical chemistry to make and use the same.

The conversion of lower-cyclic-alkylidenyl N-(2-Q-6-R'-4-pyrimidinyl)aminomethylenemalonate (II) to 2-Q-4-R'-pyrido[2,3-d]pyrimidin-5(8H)-one (III) is carried out by heating II in an inert solvent at about 225°-300° C., preferably at about 240°-270° C. Such solvents include mineral oil, diethyl phthalate, dibenzyl ether, the eutectic mixture of diphenyl and diphenyl ether (DOWTHERM ® A), and the like.

Preparation of the intermediate lower-cyclic-alkylidenyl N-(2-Q-6-R'-4-pyrimidinyl)aminomethylenemalonates is shown in said Lesher and Singh U.S. Pat. No. 4,018,770.

The reaction of 2-Q-4-R'-pyrido[2,3-d]pyrimidin-5(8H)-one (III) with an alkylating agent of the formula R-An to produce 2-Q-4-R'-8-R-pyrido[2,3-d]pyrimidin-5(8H)-one (I where Q' is hydrogen and Q is 4(or 3)-methoxyphenyl, 4(or 3)-pyridinyl or 4(or 3)-pyriidnyl having one or two lower-alkyl substituents) is carried out preferably by reacting an alkali metal salt of III with a slight excess of R-An (IV), preferably in an aprotic solvent such as dimethylformamide, where An is a leaving group corresponding to the anion of a strong inorganic acid or an organic sulfonic acid, e.g., bromide, iodide, sulfate, chloride, methanesulfonate, ethanesulfonate, benzenesulfonate, para-toluenesulfonate, and the like; chloride, bromide, iodide and sulfate are preferred because of their ready availability. The reaction is preferably run by first mixing the reactants at room temperature and then heating the reaction mixture at about 75° to 125° C., preferably about 90° to 110° C. The reaction is conveniently run by heating the reactants on a steam bath. The reaction also can be run by forming the alkali or alkaline earth metal salt of III in situ, that is, by mixing III, R-An (IV), solvent and an acid-acceptor such as sodium hydroxide, potassium hydroxide, calcium hydroxide, barium hydroxide, sodium carbonate, potassium carbonate, sodium ethoxide, potassium methoxide, sodium amide, sodium hydride, lithium hydride, calcium hydride, and the like. While the reaction is preferably run in the presence of an aprotic solvent such as dimethylformamide, dioxane, dimethyl sulfoxide, tetramethylurea, dimethylacetamide, hexamethylphosphortriamide, N-methylpyrrolidine, and the like, alternatively it can be run in other solvents such as a lower-alkanol, acetone or a mixture of solvents, e.g., a mixture of water and a lower-alkanol such as methanol, ethanol, isopropyl alcohol, and the like.

The conversion of the compounds of formula I where Q is 4(or 3)-methoxyphenyl to the compounds of formula I where Q is 4(or 3)-hydroxyphenyl is readily achieved by conventional means as illustrated hereinbelow.

The nitration of 2-Q-4-R'-8-R-pyrido[2,3-d]pyrimidin-5(8H)-one (I where Q' is hydrogen and Q is 4(or 3)-pyridinyl or 4(or 3)-pyridinyl having one or two lower-alkyl substituents) to produce the corresponding 2-Q-4-R'-6-nitro-8-R-pyrido[2,3-d]pyrimidin-5(8H)-one (I where Q' is nitro) is carried out by heating I where Q' is hydrogen up to about 100° C. with a nitrating agent such as a mixture of concentrated and/or fuming sulfuric acid and fuming nitric acid, a mixture of potassium nitrate and concentrated sulfuric acid, or other known nitrating agents.

The preparation of the 2-Q-4-R'-6-amino-8-R-pyrido[2,3-d]pyrimidin-5(8H)-one where Q is 4(or 3)-methoxy or 4(or 3)-hydroxyphenyl can be prepared from the corresponding 6-carbethoxy compound [prepared by the procedure described in said Lesher and Singh U.S. Pat. No. 3,992,380] by successive conversions using conventional means first to the corresponding 6-carbamyl compound and then to the 6-amino compound.

The reduction of said 6-nitro compound (I where Q' is nitro) to produce the corresponding 6-amino compound (I where Q' is amino) is carried out with an agent capable of reducing nitro to amino, either by catalytic hydrogenation using Pd/C, $PtO_2$ or Raney Ni catalyst or by chemical reduction, e.g., reduced iron, zinc or iron plus hydrochloric acid, stannous chloride and hydrochloric acid, and the like.

The following examples will further illustrate the invention without, however, limiting it thereto.

A. LOWER-CYCLIC-ALKYLIDENYL N-(2-Q-6-R'-4-PYRIMIDINYL)AMINOMETHYLENEMALONATES

These compounds and their preparation are generically shown and claimed in said U.S. Pat. No. 4,018,770, issued Apr. 19, 1977. Specifically shown therein (Example B-21) is the reaction of 2-(4-pyridinyl)-4-pyrimidinylamine [same as 4-amino-2-(4-pyridinyl)-pyrimidine] with cyclic isopropylidenyl malonate and triethyl orthoformate in refluxing toluene in the presence of p-toluenesulfonic acid to produce 2,2-dimethyl-5-<[2-(4-pyridinyl)-4-pyrimidinyl]amino methyl>-1,3-dioxane-2,4-dione, which is alternatively and preferably named herein as cyclic isopropylidenyl N-[2-(4-pyridinyl)-4-pyrimidinyl]aminomethylenemalonate. Alternatively, these compounds can be prepared by first reacting lower-cyclic-alkylidenyl malonate with a tri-(lower-alkyl) orthoformate to prepare lower-cyclic-alkylidenyl lower-alkoxymethylenemalonate which is then reacted with 2-Q-6-R'-4-pyrimidinamine to produce lower-cyclic-alkylidenyl N-[2-Q-6-R'-4-pyrimidinyl]aminomethylene-malonate, as illustrated hereinbelow.

A-1. Isopropylidenyl N-[2-(4-pyridinyl)-4-pyrimidinyl]aminomethylenemalonate—A mixture containing 33.8 g of 4-(4-pyridinyl)-2-pyrimidinamine and 2.3 liters of methanol was refluxed with stirring for 30 minutes and the mixture was filtered through diatomaceous earth. To the filtrate was added portionwise with stirring 36.5 g of cyclic isopropylidenyl methoxymethylenemalonate and the reaction mixture was refluxed with stirring for 10 minutes and then cooled in an ice bath. The precipitated solid was collected, washed with a small quantity of cold methanol and dried at 65° C. in vacuo to produce 58.4 g of isopropylidenyl N-[2-(4-pyridinyl)-4-pyrimidinyl]aminomethylenemalonate, m.p., 250°-251° C.

The above intermediate cyclic isopropylidenyl methoxymethylenemalonate was prepared as follows: a stirred solution containing 72 g of cyclic isopropylidenyl malonate and 26.5 g of trimethyl orthoformate was heated on a steam bath for two hours and cooled in an ice bath. Separated solid was collected, washed with n-hexane dried in vacuo at 50° C., recrystallized from methanol (total volume of about 325 ml) washed with a small quantity of cold methanol and dried in vacuo at 60° C. to yield 43.4 g of cyclic isopropylidenyl methoxymethylenemalonate, m.p. 142°-144° C.

A-2. Cyclic isopropylidene N-[2-(3-pyridinyl)-4-pyrimidinyl]aminomethylenemalonate, m.p. 245°-246° C., 4.6 g, was prepared following the procedure described in Example A-1 using 5.1 g of 4-(3-pyridinyl)-2-pyrimidinamine, 5.5 g of cyclic isopropylidenyl methoxymethylenemalonate and 150 ml of methanol.

A-3. Cyclic isopropylidene N-[2-(4-methoxyphenyl)-4-pyrimidinyl]aminomethylenemalonate, m.p. 232°–233° C., 6.5 g, was prepared following the procedure described in Example A-1 using 4.02 g of 4-(4-methoxyphenyl)-2-pyrimidinamine, 3.72 g of cyclic isopropylidenyl methoxymethylenemalonate and 50 ml of methanol.

The above intermediate 2-(4-methoxyphenyl)-4-pyrimideneamine was prepared as follows: A slurry containing 81 g of 4-methoxybenzamidine hydrochloride, 24 g of sodium methoxide and 200 ml of methanol was stirred for 15 minutes, filtered and the filtrate concentrated in vacuo on a steam bath. To the residue was added β-ethoxyacrylonitrile (same as ethoxymethyleneacetonitrile) and the solution was heated at 100°–115° C. for 2 and ½ hours and poured into water. The solid was collected, washed with water, air-dried, and crystallized from ether-n-hexane to yield 85 g of 2-(4-methoxyphenyl)-4-pyrimidinamine, m.p. 102°–104° C.

Following the procedure described in Example A-1 using in place of 2-(4-pyridinyl)-4-pyrimidinamine a molar equivalent quantity of the corresponding 2-Q-6-R'-4-pyrimidinamine, it is contemplated that the following cyclic isopropylidenyl N-(2-Q-6-R'-4-pyrimidinyl-)aminomethylenemalonates of Examples A-4 through A-9 can be obtained.

A-4. Cyclic isopropylidenyl N-[2-(4-pyridinyl)-6-methyl-4-pyrimidinyl]aminomethylenemalonate, using 2-(4-pyridinyl)-6-methyl-4-pyrimidinamine.

A-5. Cyclic isopropylidenyl N-[2-(2-methyl-4-pyridinyl)-6-pyrimidinyl]aminomethylenemalonate, using 2-(2-methyl-4-pyridinyl)-4-pyrimidinamine.

A-6. Cyclic isopropylidenyl N-[2-(3-methyl-4-pyridinyl)-6-pyrimidinyl]aminomethylenemalonate, using 2-(3-methyl-4-pyridinyl)-4-pyrimidinamine.

A-7. Cyclic isopropylidenyl N-[2-(2-ethyl-4-pyridinyl)-6-pyrimidinyl]aminomethylenemalonate, using 2-(2-ethyl-4-pyridinyl)-4-pyrimidinamine.

A-8. Cyclic isopropylidenyl N-[2-(2,6-dimethyl-4-pyridinyl)-6-pyrimidinyl]aminomethylenemalonate, using 2-(2,6-dimethyl-4-pyridinyl)-4-pyrimidinamine.

A-9. Cyclic isopropylidenyl N-[2-(4-pyridinyl)-6-n-propyl-4-pyrimidinyl]aminomethylenemalonate, using 2-(4-pyridinyl)-6-n-propyl-4-pyrimidinamine.

B.
2-Q-4-R'-PYRIDO[2,3-d]PYRIMIDIN-5(8H)-ONES

B-1. 2-(4-Pyridinyl)pyrido[2,3-d]pyrimidin-5(8H)-one—To a 600 ml portion of a eutectic mixture of diphenyl and diphenyl ether was added in four portions 15.6 g of isopropylidenyl N-[2-(4-pyridinyl)-4-pyrimidinyl]aminomethylenemalonate and the resulting reaction mixture was heated at about 245° C. for about five minutes and then allowed to cool to room temperature. The solid that separated was collected, washed with n-hexane, slurried with 600 ml of refluxing chloroform for about two hours, filtered, washed with chloroform and dried at 65° C. in vacuo to produce 6.1 g of 2-(4-pyridinyl)pyrido[2,3-d]pyrimidin-5(8H)-one. This 6.1 g portion of product was combined with another 5.2 g of the same compound obtained in another run and the combination was dissolved in 300 ml of boiling dimethylformamide, the hot solution treated with decolorizing charcoal and filtered, and the filtrate also treated with decolorizing charcoal and filtered. The filtrate was cooled in an ice bath to precipitate the product. The product was collected, washed with n-hexane and dried at 65° C. in vacuo to produce 6.2 g of 2-(4-pyridinyl)-pyrido[2,3-d]pyrimidin-5(8H)-one, m.p. >350° C.

B-2. 2-(3-Pyridinyl)pyrido[2,3-d]pyrimidin-5(8H)-one, 5.15 g, m.p. >350° C., was prepared following the procedure described in Example B-1 using 9.35 g of cyclic isopropylidenyl N-[2-(3-pyridinyl)-4-pyrimidinyl]aminomethylenemalonate, 550 ml of a eutectic mixture of diphenyl and diphenylether, and a refluxing temperature of 250° C.

B-3. 2-(4-Methoxyphenyl)pyrido[2,3-d]pyrimidin-5(8H)-one, 5.8 g, m.p. 345°–346° C., was prepared following the procedure described in Example B-1 using 11.6 g of cyclic isopropylidenyl N-[2-(4-methoxyphenyl)-4-pyrimidinyl]aminomethylenemalonate, 500 ml of a eutectic mixture of diphenyl and diphenyl ether and a refluxing temperature of 250° C.

Following the procedure described in Example B-1 using in place of isopropylidenyl N-[2-(4-pyridinyl)-4-pyrimidinyl)aminomethylenemalonate a molar equivalent quantity of the corresponding cyclic isopropylidenyl N-(2-Q-6-R'-4-pyrimidinyl)aminomethylenemalonate, it is contemplated that the following 2-Q-4-R'-pyrido[2,3-d]pyrimidin-5-(8H)-ones of Example B-4 through B-9 can be obtained.

B-4. 2-(4-Pyridinyl)-4-methylpyrido[2,3-d]pyrimidin-5(8H)-one, using cyclic isopropylidenyl N-[2-(4-pyridinyl)-6-methyl-4-pyrimidinyl]aminomethylenemalonate.

B-5. 2-(2-Methyl-4-pyridinyl)pyrido[2,3-d]pyrimidin-5(8H)-one, using cyclic isopropylidenyl N-[2-(2-methyl-4-pyridinyl)-6-pyrimidinyl]aminomethylenemalonate.

B-6. 2-(3-Methyl-4-pyridinyl)pyrido[2,3-d]pyrimidine-5(8H)-one, using cyclic isopropylidenyl N-[2-(3-methyl-4-pyridinyl)-6-pyrimidinyl]aminomethylenemalonate.

B-7. 2-(2-Ethyl-4-pyridinyl)pyrido[2,3-d]pyrimidin-5(8H)-one, using cyclic isopropylidenyl N-[2-(2-ethyl-4-pyridinyl)-6-pyrimidinyl]aminomethylenemalonate.

B-8. 2-(2,6-Dimethyl-4-pyridinyl)pyrido[2,3-d]pyrimidin-5(8H)-one, using cyclic isopropylidenyl N-[2-(2,6-dimethyl-4-pyridinyl)-6-pyrimidinyl-]aminomethylenemalonate.

B-9. 2-(4-Pyridinyl)-6-n-propylpyrido[2,3-d]pyrimidin-5(8H)-one, using cyclic isopropylidenyl N-[2-(4-pyridinyl]-6-n-propyl-4-pyrimidinyl)aminomethylenemalonate.

C.
2-Q-4-R'-6-Q'-8-R-PYRIDO[2,3-d]PYRIMIDIN-5-(8H)-ONES

C-1. 8-Ethyl-2-(4-pyridinyl)pyrido[2,3-d]pyrimidin-5(8H)-one—A mixture containing 12.7 g of 2-(4-pyridinyl)pyrido[2,3-d]pyrimidin-5(8H)-one, 2.74 g of 50% sodium hydride in mineral oil and 300 ml of dimethylformamide was stirred at room temperature until evolution of hydrogen ceased. The mixture was heated gently with stirring on a steam bath for 30 minutes, one drop diisopropylamine was added followed by 100 mg of sodium hydride and gentle heating with stirring was continued for another 45 minutes. The mixture was then cooled to room temperature and to it was added dropwise with stirring at room temperature 8.85 g of ethyl iodide. The reaction mixture was stirred at room temperature for three hours and then heated gently with stirring on a steam bath for 30 minutes. The solvent was then distilled off in vacuo and the residue was shaken well with a mixture of water and chloroform. The water layer was extracted several times with chloroform and the chloroform extracts were combined with the chloroform layer. The combined chloroform solution was dried over anhydrous sodium sulfate, the mixture filtered, and the filtrate treated with decolorizing charcoal and filtered. The chloroform was distilled off in vacuo and the remaining 12 g of solid residue was dissolved in 300 ml of hot isopropyl alcohol, the hot alcohol solution treated with decolorizing charcoal and filtered. The filtrate was concentrated to a volume of about 150 ml and cooled. The precipitated solid was collected, washed with a small quantity of cold isopropyl alcohol, and dried at 65° C. in vacuo to produce 6.8 g of 8-ethyl-2-(4-pyridinyl)pyrido[2,3-d]pyrimidin-5(8H)-one, m.p. 200°–202° C. Additional product was obtained from the mother liquor.

Acid-addition salts of 8-ethyl-2-(4-pyridinyl)-pyrido[2,3-d]pyrimidin-5(8H)-one are conveniently prepared by adding to a mixture of 1 g of 8-ethyl-2-(4-pyridinyl)pyrido[2,3-d]pyrimidin-5(8H)-one in about 20 ml of aqueous methanol the appropriate acid, e.g., hydrochloric acid, methanesulfonic acid, concentrated sulfuric acid, concentrated phosphoric acid, to a pH of about 2 to 3, chilling the mixture after partial evaporation and collecting the precipitated salt, e.g., hydrochloride, methanesulfonate, sulfate, phosphate, respectively. Also, the acid-addition salt is conveniently prepared in aqueous solution by adding to water with stirring a molar equivalent quantity each of 8-ethyl-2-(4-pyridinyl)pyrido[2,3-d]pyrimidin-5(8H)-one and the appropriate acid, e.g., lactic acid or hydrochloric acid, to prepare respectively the lactate or hydrochloride salt of 8-ethyl-2-(4-pyridinyl)pyrido[2,3-d]pyrimidin-5(8H)-one in aqueous solution.

C-2. 8-Ethyl-2-(3-pyridinyl)pyrido[2,3-d]pyrimidin-5(8H)-one—A mixture containing 8.7 g of 2-(3-pyridinyl)pyrido[2,3-d]pyrimidin-5(8H)-one, 1.9 g of 50% sodium hydride in mineral oil and 250 ml of dimethylformamide was stirred at room temperature until evolution of hydrogen ceased. To the mixture was added an additional 50 ml of dimethylformamide and gentle heating was continued on a steam bath for 30 minutes. The mixture was cooled to room temperature and to it was added one drop of diisopropyl amine with stirring followed by an additional 100 mg of sodium hydride. Gentle heating with stirring was continued for another 30 minutes followed by cooling to room temperature. To the mixture was added with stirring at room temperature 6.1 g of ethyl iodide slowly in a fine stream and resulting reaction mixture was stirred at room temperature for three hours and then heated gently with stirring on a steam bath for four hours. The reaction mixture was then distilled in vacuo to remove the solvent and any other volatile materials and the residue was taken up and shaken well with a mixture of chloroform and water. The layers were separated and the chloroform layer was dried over anhydrous sodium sulfate, treated with decolorizing charcoal and filtered, and the filtrate was distilled in vacuo to remove the chloroform. The residue was dissolved in 150 ml of boiling acetonitrile: the resulting hot solution was treated with decolorizing charcoal and filtered; and, the filtrate was concentrated to a volume of 100 ml and cooled to complete precipitation of the product. The product was collected, washed successively with a small quantity of acetonitrile and n-hexane, and dried in vacuo at 65° C. to yield 6.5 g of 8-ethyl-2-(3-pyridinyl)-pyrido[2,3-d]pyrimidin-5(8H)-one, m.p. 195°–196° C.

Acid-addition salts of 8-ethyl-2-(3-pyridinyl)-pyrido[2,3-d]pyrimidin-5(8H)-one are conveniently prepared by adding to a mixture of 1 g of 8-ethyl-2-(3-pyridinyl)pyrido[2,3-d]pyrimidin-5(8H)-one in about 20 ml of aqueous methanol the appropriate acid, e.g., hydrochloric acid, methanesulfonic acid, concentrated sulfuric acid, concentrated phosphoric acid, to a pH of about 2 to 3, chilling the mixture after partial evaporation and collecting the precipitated salt, e.g., hydrochloride, methanesulfonate, sulfate, phosphate, respectively. Also, the acid-addition salt is conveniently prepared in aqueous solution by adding to water with stirring a molar equivalent quantity each of 8-ethyl-2-(3-pyridinyl)pyrido[2,3-d]pyrimidin-5(8H)-one and the appropriate acid, e.g., lactic acid or hydrochloric acid, to prepare respectively the lactate or hydrochloride salt of 8-ethyl-2-(3-pyridinyl)pyrido[2,3-d]pyrimidin-5(8H)-one in aqueous solution.

C-3. 8-Ethyl-2-(4-methoxyphenyl)pyrido[2,3-d]pyrimidin-5(8H)-one, 9.1 g, m.p. 220°–223° C., was prepared following the procedure described in Example C-2 in two runs using 6.0 and 12.25 g of starting material, e.g, 2-(4-methoxyphenyl)pyrido[2,3-d]pyrimidin-5(8H)-one, and recrystallizing the combined products from absolute ethanol.

C-4. 8-Ethyl-2-(4-hydroxyphenyl)pyrido[2,3-d]pyrimidin-5(8H)-one—A mixture containing 2.4 g of 8-ethyl-2-(4-methoxyphenyl)pyrido[2,3-d]pyrimidin-5(8H)-one, 8.1 g of anhydrous lithium iodide, 125 ml of collidine and one drop of dicyclohexyl-12-crown-4 was refluxed with stirring for 24 hours and then allowed to cool to room temperature. The reaction mixture was diluted with n-hexane (900 ml) to complete the precipitation of the product. The oily material that separated solidified on standing at room temperature. The solid was collected, washed with n-hexane and then dissolved in water. The water solution and washed with ether, acidified with hydrochloric acid and the resulting mixture was slurried, treated with an excess of sodium bicarbonate and again slurried. The solid was collected, washed with water and dried at 65° C. in vacuo to yield 1.85 g of 8-ethyl-2-(4-hydroxyphenyl)pyrido[2,3-d]pyrimidin-5(8H)-one, m.p. 320°–324° C. This product was combined with 12 g of product obtained in five other runs and the combined material was suspended in about 350 ml of boiling ethanol after which dimethylformamide was added portionwise until dissolution was complete. The hot solution was treated with decolorizing charcoal, filtered, and the filtrate cooled. The separated product was collected, washed with cold ethanol and dried in vacuo at 60° C. to produce 2.6 g of 8-ethyl-2-(4-hydroxyphenyl)pyrido[2,3-d]pyrimidin-5(8H)-one, m.p. 323°–325° C. The filtrate was stripped in vacuo, the solid residue was recrystallized from ethanoldimethylformamide to yield another 0.8 g of product, 8-ethyl-2-(4-hydroxyphenyl)pyrido[2,3-d]pyrimidin-5(8H)-one, m.p. 321°–322° C.

C-5. 8-n-Propyl-2-(4-pyridinyl)pyrido[2,3-d]pyrimidin-5(8H)-one, 4.7 g, m.p. 180°–181° C., was obtained following the procedure described in Example C-2 using 11.2 g of 2-(4-pyridinyl)pyrido[2,3-d]pyrimidin-5(8H)-one, 300 ml of dimethylformamide, 2.4 g of 50% sodium hydride in mineral oil, 8.5 g of n-propyl iodide, a heating period of twelve hours, and recrystallization from isopropyl alcohol using decolorizing charcoal.

C-6. 8-n-Butyl-2-(4-pyridinyl)pyrido[2,3-d]pyrimidin-5(8H)-one, 8.3 g, m.p. 160°–161° C., was obtained following the procedure described in Example C-2 using 13.1 g of 2-(4-pyridinyl)pyrido[2,3-d]pyrimidin-5(8H)-one, 300 ml of dimethylformamide, 2.8 g of 50% sodium hydride in mineral oil, 10.8 g of n-butyl iodide, a heating period of seven hours, and recrystallization from isopropyl alcohol using decolorizing charcoal.

C-7. 8-n-Butyl-2-(3-pyridinyl)pyrido[2,3-d]pyrimidin-5(8H)-one, 5.7 g, m.p. 133°–135° C., was prepared following the procedure described in Example C-2 using 9.3 g of 2-(3-pyridinyl)pyrido[2,3-d]pyrimidin-5(8H)-one, 250 ml of dimethylformamide, 2.0 g of 50% sodium hydride in mineral oil, 7.65 g of n-butyl iodide, a heating period of eight hours, and recrystallization from isopropyl alcohol using decolorizing charcoal.

C-8. 8-n-Butyl-6-nitro-2-(4-pyridinyl)pyrido[2,3-d]pyrimidin-5(8H)-one—To 7.2 g of concentrated sulfuric acid was added, with stirring and cooling keeping the temperature below 30° C., 10.8 ml of fuming sulfuric acid. To the resulting mixture was added 6.0 ml of fuming nitric acid with stirring, and cooling as necessary to keep the temperature below 30° C. To the stirred mixture of acids at room temperature was added 6.6 g of 8-n-butyl-2-(4-pyridinyl)pyrido[2,3-d]pyrimidin-5(8H)-one. The reaction mixture was heated with stirring, gradually raising the temperature to 90° over a twenty minute period and then maintaining the reaction mixture at 90°–95° C. for ten minutes. The reaction mixture was cooled to 30° C. and added to 500 ml of a mixture of ice and water. The resulting mixture was made basic by adding concentrated ammonium hydroxide and the resulting mixture was allowed to stand for one hour. The separated solid was collected, washed with water, dried at 65° C. in vacuo to produce 6.3 g of 8-n-butyl-6-nitro-2-(4-pyridinyl)pyrido[2,3-d]pyrimidin-5(8H)-one, m.p. 240°–241° C. The product was dissolved in 50 ml of boiling dimethylformamide, the solution treated with decolorizing charcoal and filtered, and the filtrate concentrated to a volume of about 30 ml and cooled to complete precipitation of the product. The product was collected, washed with a small quantity of cold ethanol, and dried at 65° C. in vacuo to produce 5.25 g of 8-n-butyl-6-nitro-2-(4-pyridinyl)pyrido[2,3-d]pyrimidin-5(8H)-one, m.p. 241°–243° C.

C-9. 6-Amino-8-n-butyl-2-(4-pyridinyl)pyrido[2,3-d]pyrimidin-5(8H)-one—A stirred mixture containing 400 ml of absolute methanol, 80 ml of water, 1 ml of concentrated hydrochloric acid and 8.6 g of reduced iron was brought to a boil in an 800 ml beaker on a steam bath. The heat was removed and to the mixture was added portionwise with stirring 7.95 g of 8-n-butyl-6-nitro-2-(4-pyridinyl)pyrido[2,3-d]pyrimidin-5(8H)-one and the reaction mixture was then boiled with stirring for 30 minutes. To the reaction mixture was added portionwise 8.0 g of sodium bicarbonate and the resulting mixture was boiled with stirring for an additional 10 minutes, during which time additional absolute ethanol was added intermittently to maintain constant volume. The hot reaction mixture was filtered through diatomaceous earth and the pad washed with hot ethanol. The filtrate was heated in vacuo to remove the solvent and other volatile materials. The residue was taken up in 100 ml of chloroform and the chloroform solution was dried over anhydrous sodium sulfate, the mixture filtered and the filtrate stripped in vacuo to produce 7.3 g of solid, m.p. 193°–195° C. The solid was combined with another 0.9 g of the corresponding solid prepared in another run and the mixture was dissolved in 200 ml of boiling isopropyl alcohol, the volume concentrated to 100 ml and cooled to complete precipitation of the product. The solid was collected, washed with cold isopropyl alcohol and dried at 65° C. in vacuo to produce 7.2 g of 6-amino-8-n-butyl-2-(4-pyridinyl)pyrido[2,3-d]pyrimidin-5(8H)-one, m.p. 195°–196° C.

Acid-addition salts of 6-amino-8-n-butyl-2-(4-pyridinyl)pyrido[2,3-d]pyrimidin-5(8H)-one are conveniently prepared by adding to a mixture of 1 g of 6-amino-8-n-butyl-2-(4-pyridinyl)pyrido[2,3-d]pyrimidin-5(8H)-one in about 20 ml of aqueous methanol the appropriate acid, e.g., hydrochloric acid, methanesulfonic acid, concentrated sulfuric acid, concentrated phosphoric acid, to a pH of about 2 to 3, chilling the mixture after partial evaporation and collecting the precipitated salt, e.g., hydrochloride, methanesulfonate, sulfate, phosphate, respectively. Also, the acid-addition salt is conveniently prepared in aqueous solution by adding to water with stirring a molar equivalent quantity each of 6-amino-8-n-butyl-2-(4-pyridinyl)pyrido[2,3-d]pyrimidin-5(8H)-one and the appropriate acid, e.g., lactic acid or hydrochloric acid, to prepare respectively the lactate or hydrochloride salt of 6-amino-8-n-butyl-2-(4-pyridinyl)pyrido[2,3-d]pyrimidin-5(8H)-one in aqueous solution.

C-10. 8-(1-Ethylpropyl)-2-(4-pyridinyl)pyrido[2,3-d]pyrimidin-5(8H)-one, 5.0 g, m.p. 157°–160° C., was prepared following the procedure described in Example C-2 using 11.2 g of 2-(4-pyridinyl)pyrido[2,3-d]pyrimidin-5(8H)-one, 300 ml of dimethylformamide, 2.4 g of 50% sodium hydride in mineral oil, 9.9 g of 3-pentyl iodide, a heating period of 19 hours, and recrystallization from isopropyl acetate using decolorizing charcoal.

C-11. 8-(3-Butenyl)-2-(4-pyridinyl)pyrido[2,3-d]pyrimidin-5(8H)-one, 4.2 g, m.p. 141°–143° C., was prepared following the procedure described in Example C-2 using 8.2 g of 2-(4-pyridinyl)pyrido[2,3-d]pyrimidin-5(8H)-one, 250 ml of dimethylformamide, 1.75 g of 50% sodium hydride in mineral oil, 4.93 g of 3-butenyl bromide, a heating period of 19 hours, recrystallization from isopropyl alcohol using decolorizing charcoal and a second recrystallization from isopropyl alcohol.

C-12. 8-Isopropyl-2-(4-pyridinyl)pyrido[2,3-d]pyrimidin-5(8H)-one, 5.6 g, m.p. 269°–271° C., was prepared following the procedure described in Example C-2 using 11.2 g of 2-(4-pyridinyl)pyrido[2,3-d]pyrimidin-5(8H)-one, 300 ml of dimethylformamide, 2.4 g of 50% sodium hydride in mineral oil, 8.5 g of isopropyl iodide, a heating period of 24 hours and two recrystallizations from isopropyl alcohol.

C-13. 8-(2-Methoxyethyl)-2-(4-pyridinyl)pyrido[2,3-d]pyrimidin-5(8H)-one, 4.0 g, m.p. 202°–203° C., was prepared following the procedure described in Example C-2 using 8 g of 2-(4-pyridinyl)pyrido[2,3-d]pyrimidin-5(8H)-one, 250 ml of dimethylformamide, 1.72 g of 50% sodium hydride in mineral oil, 5 g of 2-methoxyethyl bromide, a heating period of 18 hours and two recrystallizations from absolute ethanol.

C-14. 8-Methyl-2-(4-pyridinyl)pyrido[2,3-d]pyrimidin-5(8H)-one, 5.0 g, m.p. 266°–268° C., was prepared following the procedure described in Example C-2 using 12.35 g of 2-(4-pyridinyl)pyrido[2,3-d]pyrimidin-5(8H)-one, 300 ml of dimethylformamide, 2.65 g of 50% sodium hydride in mineral oil, 7.8 g of methyl iodide, a heating period of 30 minutes, and two recrystallizations from ethanol using decolorizing charcoal.

C-15. 8-(2-Hydroxyethyl)-2-(4-pyridinyl)pyrido[2,3-d]pyrimidin-5(8H)-one, 4.7 g, m.p. 250°–252° C., was prepared following the procedure described in Example C-2 using 12.35 g of 2-(4-pyridinyl)pyrido[2,3-d]pyrimidin-5(8H)-one, 300 ml of dimethylformamide, 2.65 g of 50% sodium hydride in mineral oil, 9.5 g of 2-hydroxyethyl iodide, a heating period of seven hours, and recrystallization from absolute ethanol using decolorizing charcoal.

C-16. 8-(3-Hydroxypropyl)-2-(4-pyridinyl)-pyrido[2,3-d]pyrimidin-5(8H)-one, 4.2 g, m.p. 198°-201° C., was prepared following the procedure described in Example C-2 using 10.0 g of 2-(4-pyridinyl)pyrido[2,3-d]pyrimidin-5(8H)-one, 250 ml of dimethylformamide, 2.12 g of 50% sodium hydride in mineral oil, 6.2 g of 3-hydroxypropyl bromide, a heating period of 18 hours, and two recrystallizations from isopropyl alcohol.

C-17. 8-(2-Dimethylaminoethyl)-2-(4-pyridinyl)-pyrido[2,3-d]pyrimidin-5(8H)-one, 4.9 g, m.p. 157°-159° C., was prepared following the procedure described in Example C-2 using 8.0 g of 2-(4-pyridinyl)pyrido[2,3-d]pyrimidin-5(8H)-one, 250 ml of dimethylformamide, 1.72 g of 50% sodium hydride in mineral oil, 3.86 g of 2-dimethylaminoethyl chloride, a heating period of eight hours, and recrystallization from isopropyl acetate using decolorizing charcoal.

Following the procedure described in Example C-2 but using in place of 2-(3-pyridinyl)-pyrido[2,3-d]pyrimidin-5(8H)-one and ethyl iodide corresponding molar equivalent quantities of the appropriate 2-Q-4-R'-pyrido[2,3-d]pyrimidin-5(8H)-one and alkylating agent of the formula R-An, it is contemplated that the corresponding products of Examples C-18 thru C-25 can be obtained.

C-18. 8-Ethyl-4-methyl-2-(4-pyridinyl)pyrido[2,3-d]pyrimidin-5(8H)-one, using 4-methyl-2-(4-pyridinyl)-pyrido[2,3-d]pyrimidin-5(8H)-one and ethyl iodide.

C-19. 8-Ethyl-2-(2-methyl-4-pyridinyl)pyrido[2,3-d]pyrimidin-5(8H)-one, using 2-(2-methyl-4-pyridinyl)-pyrido[2,3-d]pyrimidin-5(8H)-one and ethyl bromide.

C-20. 8-n-Butyl-2-(3-methyl-4-pyridinyl)pyrido[2,3-d]pyrimidin-5(8H)-one and n-butyl bromide.

C-21. 2-(2-Ethyl-4-pyridinyl)-8-n-propylpyrido[2,3-d]pyrimidin-5(8H)-one, using 2-(2-ethyl-4-pyridinyl)-pyrido[2,3-d]pyrimidin-5(8H)-one and n-propyl iodide.

C-23. 8-Ethyl-2-(2,6-dimethyl-4-pyridinyl)pyrido[2,3-d]pyrimidin-5(8H)-one, using 2-(2,6-dimethyl-4-pyridinyl)pyrido[2,3-d]pyrimidin-5(8H)-one and ethyl iodide.

C-24. 8-Ethyl-4-n-propyl-2-(4-pyridinyl)pyrido[2,3-d]pyrimidin-5(8H)-one, using 4-n-propyl-2-(4-pyridinyl)pyrido[2,3-d]pyrimidin-5(8H)-one and ethyl bromide.

C-25. 8-Allyl-2-(4-pyridinyl)pyrido[2,3-d]pyrimidin-5(8H)-one, using 2-(4-pyridinyl)pyrido[2,3-d]pyrimidin-5(8H)-one and allyl bromide.

Following the procedure described in Example C-8 but using in place of 8-n-butyl-2-(4-pyridinyl)pyrido[2,3-d]pyrimidin-5(8H)-one a molar equivalent quantity of the appropriate 2-Q-4-R'-8-R-pyrido[2,3-d]pyrimidin-5(8H)-one, it is contemplated that the following 6-nitro compounds of Examples C-26 thru C-29 can be obtained.

C-26. 8-Ethyl-6-nitro-2-(2-methyl-4-pyridinyl)-pyrido[2,3-d]pyrimidin-5(8H)-one, using 8-ethyl-2-(2-methyl-4-pyridinyl)pyrido[2,3-d]pyrimidin-5(8H)-one.

C-27. 4-Methyl-6-nitro-8-n-propyl-2-(4-pyridinyl)-pyrido[2,3-d]pyrimidin-5(8H)-one, using 4-methyl-8-n-propyl-2-(4-pyridinyl)pyrido[2,3-d]pyrimidin-5(8H)-one.

C-28. 2-(2-Ethyl-4-pyridinyl)-6-nitro-8-n-propyl-pyrido[2,3-d]pyrimidin-5(8H)one, using 2-(2-ethyl-4-pyridinyl)-8-n-propylpyrido[2,3-d]pyrimidin-5(8H)-one.

C-29. 8-Ethyl-2-(2,6-dimethyl-4-pyridinyl)-6-nitropyrido[2,3-d]pyrimidin-5(8H)-one using 8-ethyl-2-(2,6-dimethyl-4-pyridinyl)pyrido[2,3-d]pyrimidin-5(8H)-one.

Following the procedure described in Example C-9 but using in place of 8-n-butyl-6-nitro-2-(4-pyridinyl)-pyrido[2,3-d]pyrimidin-5(8H)-one a corresponding molar equivalent quantity of the corresponding 2-Q-4-R'-6-nitro-8-R-pyrido[2,3-d]pyrimidin-5(8H)-one, it is contemplated that the corresponding 6-amino compounds of Examples C-30 thru C-33 can be obtained.

C-30. 6-Amino-8-ethyl-2-(2-methyl-4-pyridinyl)-pyrido[2,3-d]pyrimidin-5(8H)-one, using 8-ethyl-2-(2-methyl-4-pyridinyl-6-nitropyrido[2,3-d]pyrimidin-5(8H)-one.

C-31. 6-Amino 4-methyl-8-n-propyl-2-(4-pyridinyl)-pyrido[2,3-d]pyrimidin-5(8H)-one, using 4-methyl-6-nitro-8-n-propyl-2-(4-pyridinyl)pyrido[2,3-d]pyrimidin-5(8H)-one.

C-32. 6-Amino-2-(2-ethyl-4-pyridinyl)-8-n-propyl-pyrido[2,3-d]pyrimidin-5(8H)-one, using 2-(2-ethyl-4-pyridinyl)-6-nitro-8-n-propylpyrido[2,3-d]pyrimidin-5(8H)-one.

C-33. 6-Amino-8-ethyl-2-(2,6-dimethyl-4-pyridinyl)-pyrido[2,3-d]pyrimidin-5(8H)-one, using 8-ethyl-6-nitro-2-(2,6-dimethyl-4-pyridinyl)pyrido[2,3-d]pyrimidin-5(8H)-one.

C-34. 8-Ethyl-2-(3-methoxyphenyl)pyrido[2,3-d]pyrimidin-5(8H)-one can be prepared following the procedure described in Example C-2 using in place of 2-(3-pyridinyl)pyrido[2,3-d]pyrimidin-5(8H)-one, a molar equivalent quantity of 2-(3-methoxyphenyl)-pyrido[2,3-d]pyrimidin-5(8H)-one.

C-35. 8-Ethyl-2-(3-hydroxyphenyl)pyrido[2,3-d]pyrimidin-5(8H)-one can be prepared following the procedure described in Example C-4 but using in place of 8-ethyl-2-(4-methoxyphenyl)pyrido[2,3-d]pyrimidin-5(8H)-one, a molar equivalent quantity of the corresponding 8-ethyl-2-(3-methoxyphenyl)pyrido[2,3-d]pyrimidin-5(8H)-one.

We claim:

1. 2-Q-4-R'-pyrido[2,3-d]pyrimidin-5(8H)-one having the formula

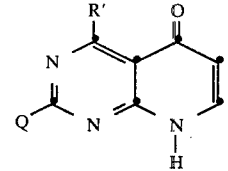

or acid-addition or alkali or alkaline earth metal salt thereof, where Q is 4(or 3)-hydroxyphenyl, 4(or 3)-methoxyphenyl, 4(or 3)-pyridinyl or 4(or 3)-pyridinyl having one or two lower-alkyl substituents, and R' is hydrogen or alkyl having from one to four carbon atoms.

2. A compound according to claim 1 where R' is hydrogen or methyl, and Q is 4(or 3)-pyridinyl.

3. 2-(4-Pyridinyl)pyrido[2,3-d]pyrimidin-5(8H)-one according to claim 1 or acid-addition or alkali or alkaline earth metal salt thereof.

4. 2-(3-Pyridinyl)pyrido[2,3-d]pyrimidin-5(8H)-one according to claim 1 or acid-addition or alkali or alkaline earth metal salt thereof.

5. 2-(4-Methoxyphenyl)pyrido[2,3-d]pyrimidin-5(8H)-one according to claim 1 or acid-addition or alkali or alkaline earth metal salt thereof.

* * * * *